United States Patent [19]
Nickell

[11] 3,989,505
[45] Nov. 2, 1976

[54] USE OF POLYCYCLIC THIOPHENE COMPOUNDS AS RIPENERS FOR SUGARCANE

[75] Inventor: Louis G. Nickell, Honolulu, Hawaii

[73] Assignee: Hawaiian Sugar Planters' Association, Honolulu, Hawaii

[22] Filed: June 23, 1975

[21] Appl. No.: 589,400

[52] U.S. Cl. .......................................... 71/90; 71/88; 260/329 R; 260/329 S; 260/329 F; 260/332.2 R; 260/332.2 C
[51] Int. Cl.² .......................................... A01N 5/00
[58] Field of Search .................................. 71/90, 88

[56] References Cited
UNITED STATES PATENTS

| | | | |
|---|---|---|---|
| 2,929,702 | 3/1960 | Speziale | 71/88 X |
| 3,705,910 | 12/1972 | Lundberg, Jr. et al. | 71/90 X |
| 3,823,161 | 7/1974 | Lesser | 71/90 X |
| 3,828,001 | 8/1974 | Broad et al. | 71/90 X |

*Primary Examiner*—Joseph P. Brust
*Attorney, Agent, or Firm*—Burns, Doane, Swecker & Mathis

[57] ABSTRACT

Sucrose yield of sugarcane is increased by treating the cane crop a few weeks prior to harvest with a certain type of polycyclic thiophene compound of the formula

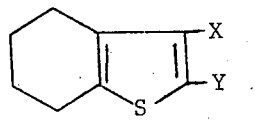

wherein X is cyano, carboalkoxy or carbamido and Y is an amino or substituted amino group, or with mixtures comprising one or more such compounds.

11 Claims, No Drawings

USE OF POLYCYCLIC THIOPHENE COMPOUNDS AS RIPENERS FOR SUGARCANE

CROSS-REFERENCE TO RELATED CASE

This application is a companion of commonly owned application of J. V. Karabinos and L. G. Nickell, Ser. No. 589,401, filed June 23, 1975, which discloses the compositions of matter which are useful as the active agents in the practice of the presently claimed invention.

FIELD OF THE INVENTION

This invention relates to an improvement in the production of sugar from sugarcane. More particularly it relates to a process for increasing the sugar yield of sugarcane by the application of certain thiophene compounds of the formula

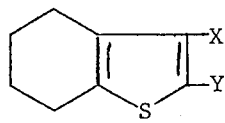

to the maturing sugarcane plants in the field a few weeks prior to harvest; it also relates to compositions of matter useful for this purpose.

THE PRIOR ART

A considerable number of a wide variety of chemical compounds have been previously proposed for use as chemical ripeners for sugarcane. Some of these are disclosed, for example, in U.S. Pat. Nos. 3,224,865; 3,245,775; 3,291,592; 3,482,959; 3,482,961; 3,493,361; 3,505,056; 3,660,072 and 3,671,219. Still other chemical agents which have been found successful or shown promise as sugarcane ripeners, such as cyclo-leucine, anisomycin and cycloheximide, are disclosed, for instance, in Hawaiian Planters' Record, Vol. 58, No. 5, pp. 71–79 (1970). A number of condensed thiophene derivatives have previously been prepared by other workers and proposed for use as dyes or dye intermediates (see, for instance, U.S. Pat. No. 3,555,016), as herbicides (see, for instance, U.S. Pat. Nos. 2,634,200; 3,705,910 and 3,823,161), or as pharmaceutical agents (see, for instance, U.S. Pat. No. 3,758,476).

Various methods of chemical synthesis used in preparing such compounds are described in these patents as well as elsewhere in the literature. For instance, the preparation of 2-amino-3-cyanotetramethylenethiophene, which is the basic starting material from which the ripening agents used in the present invention can be prepared, has been previously described by K. Gewald in Z. Chem. 2, 305 (1962); Angew. Chem. 73, 114 (1961). Other references which describe the preparation and reactions of various condensed thiophene derivatives include K. Gewald, Ber. 98, 3571 (1965); E. C. Taylor et al, Angew. Chem. 78, 144 (1966); Int. Ed. (English) 5, 131 (1966); K. Gewald et al, Ber. 99, 94 (1966); A. M. Chacko, Ph. Dissert., Univ. of North Carolina 1965, microfilm 65-14320 Ann Arbor, Michigan; and V. P. Arya, Indian J. of Chem. 10, 1141 (1972).

However, none of these compounds has previously been proposed for use as a ripener for sugarcane, and the effectiveness of the presently disclosed compounds for this purpose is entirely unexpected.

As is well known in the art, the more active ripeners differ widely from each other in terms of chemical structure as well as chemical and biological properties. As of this date there is still no known screening test for determining the ripening activity of a compound other than to test it on maturing sugarcane, and in the continuing search for effective ripeners failures continue to outnumber successes by a wide margin. Nevertheless, the search for new sugarcane ripeners continues unabated, because of toxicological or ecological concerns and the consequent possibility that rotation of use of different chemical ripeners in consecutive seasons in a given area may be preferable to the continued use of a single ripener or ripener mixture.

OBJECTS OF THE INVENTION

It is an object of this invention to provide new and economically useful chemical ripening agents for sugarcane. A more general object is to increase the sucrose yield of sugarcane by chemically treating it during its maturation prior to harvest without introducing objectionable toxicological hazards. More specifically, it is an object of this invention to increase the sucrose yield of maturing sugarcane by treating to cane crop nearing its normal harvest time with one or more condensed thiophene derivatives which are sufficiently stable to provide the desired effect over a period of several weeks between application and a variable harvest date, but yet have a relatively low degree of persistence and are susceptible to autodecomposition or to decomposition by soil bacteria. A compound which increases the sucrose content only temporarily over a period of three weeks or less after application and then results in a substantial decrease is usually not a desirable chemical ripener except in situations where harvesting time can be rigidly programmed in advance in relation to the time of application of the chemical ripener.

SUMMARY AND GENERAL DESCRIPTION OF THE INVENTION

According to the present invention the desired objectives have been achieved by the application of ripening compositions comprising a condensed thiophene compound of the general formula

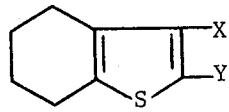

wherein X is cyano, a $C_1 - C_4$ carboalkoxy or a carbamido group, and Y is an amino radical -$NH_2$ or a radical having the formula

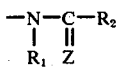

in which radical $R_1$ is hydrogen or methyl, Z is oxygen or sulfur and $R_2$ is $C_1 - C_4$ alkyl optionally substituted by chlorine, bromine or fluorine, such as methyl, ethyl, butyl, chloromethyl, 2-chloroethyl or 3-chloropropyl; or

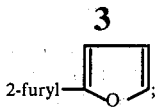

or a $C_1 - C_4$ alkyl, $C_1 - C_4$ alkoxy, halogen or $C_1 - C_4$ haloalkyl substituted phenylamino group, such as

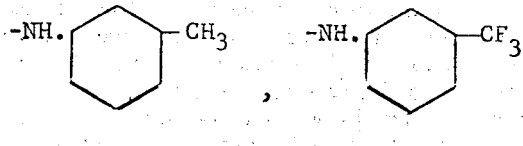

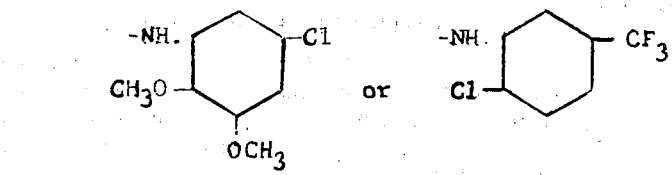

Specific compounds which are illustrative of the scope of this invention are:

2-amino-3-cyano-4,5-tetramethylenethiophene
2-amino-3-carboethoxy-4,5-tetramethylenethiophene
2-amino-3-carbamido-4,5-tetramethylenethiophene
2-acetamido-3-cyano-4,5-tetramethylenethiophene
2-trichloracetamido-3-cyano-4,5-tetramethylenethiophene
2-propionamido3-cyano-4,5-tetramethylenethiophene
2-(3-chloropropionamido)-3-cyano-4,5-tetramethylenethiophene
2-butyramido-3-cyano-4,5-tetramethylenethiophene
2-benzamido-3-cyano-4,5-tetramethylenethiophene
2-(furan-2-carbamido)-3-cyano-4,5-tetramethylenethiophene
2-acetamido-3-carboethoxy-4,5-tetramethylenethiophene
2-(2-chloroacetamido)-3-carboethoxy-4,5-tetramethylenethiophene
2-propionamido-3-carboethoxy-4,5-tetramethylenethiophene
2-(3-chloropropionamido)-3-carboethoxy-4,5-tetramethylenethiophene
2-butyramido-3-carboethoxy-4,5-tetramethylenethiophene
2-benzamido-3-carboethoxy-4,5-tetramethylenethiophene
2-(furan-2-carbamido)-3-carboethoxy-4,5-tetramethylenethiophene
2-butylureido-3-cyano-4,5-tetramethylenethiophene
2-phenylureido-3-cyano-4,5-tetramethylenethiophene
2-(5-chloro-2,4-dimethoxyphenyl)-thioureido-3-cyano-4,5-tetramethylenethiophene
2-(3-chlorophenyl)-ureido-3-cyano-4,5tetramethylenethiophene
2-(4-fluorophenyl)-ureido-3-cyano-4,5-tetramethylenethiophene
2-butylureido-3-carboethoxy-4,5-tetramethylenethiophene
2-phenylureido-3-carboethoxy-4,5-tetramethylenethiophene
2-(3-chlorophenyl)-ureido-3-carboethoxy-4,5-tetramethylenethiophene
2-(4-fluorophenyl)-ureido-3-carboethoxy-4,5-tetramethylenethiophene
2-(2-methoxy-5-methylphenyl)-ureido-3-carboethoxy-4,5-tetramethylenethiophene
2-(2-chloro-5-trifluoromethylphenyl)-ureido-3-carboethoxy-4,5-tetramethylenethiophene
2-(3-trifluoromethylphenyl)-ureido-3-carboethoxy-4,5-tetramethylenethiophene The thioureido derivatives, i.e., derivatives of some of the isothiocynates, which have been preliminarily tested to date have tended to be less active than analogous compounds of the other types listed above. Nevertheless, some of the thioureido derivatives have shown themselves to be excellent ripeners for sugarcane and may have valuable properties for other agricultural uses.

More specifically, an excellent increase in sucrose yield has been obtained by applying a liquid or dust composition comprising one or more of such condensed thiophene compounds to maturing sugarcane stalks in a crop near the end of its normal maturation cycle, and harvesting such a crop some weeks later. The composition is applied directly to the stalks by spraying, dusting or the like in order that it be deposited on the stalks including the younger, growing parts thereof. The normal maturation cycle of sugarcane under conditions such as those prevailing in Hawaii is from about 18 to about 36 months, though in some areas sugarcane is ripe and ready for harvest in 9 to 12 months.

The preferred usage form is a mixture containing the condensed thiophene compound in an aqueous solution or suspension utilizing one or a combination of known surface active agents commonly and variously used in the prior art as wetting agents, detergents or emulsifying agents. However, dry dusting compositions containing the condensed thiophene compound and a solid diluent such as clay are also useful.

All the compounds which are useful in the present invention can be derived from 2-amino-3-cyano-4,5-tetramethylenethiophene. This precursor, which has a melting point of 147–8° C., is hereinafter referred to as compound (I) and can be prepared from cyclohexanone, malononitrile, an amine such as triethylamine and sulfur by the following series of reactions, as is more fully described in the literature.

In accordance with otherwise well-known methods, the cyano group of compound (I) can be readily converted to a carboalkoxy group by reaction with a suitable alcohol under esterification conditions, e.g., by refluxing in absolute ethanol with HCl catalyst. In this manner, 2-amino-3-carboethoxy-4,5-tetramethylenethiophene is produced. Another method for preparing this amino-ester is disclosed, for instance, in U.S. Pat. No. 3,705,910, column 3.

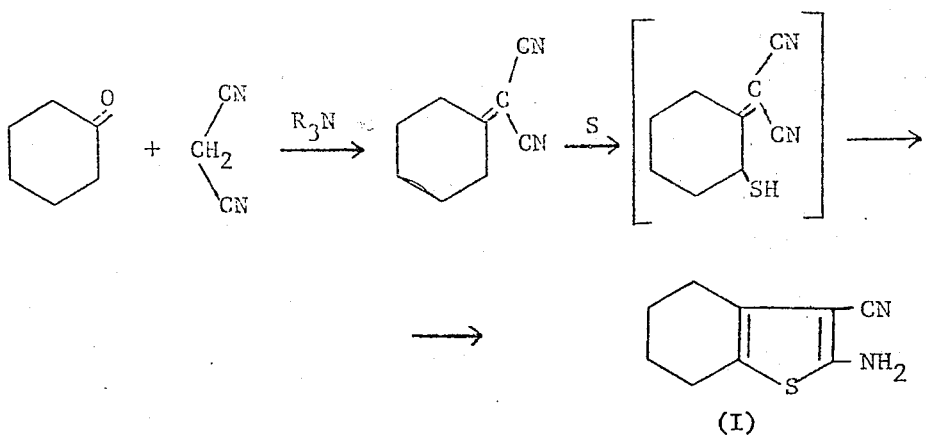

This amino-ester, hereinafter referred to as compound (II), has a melting point of 99°–101° C. and is itself suitable for use as a ripening agent for sugarcane. It is also useful as a starting material for the preparation of other derivatives by reaction of the amino group with appropriate reactants, whereby other effective ripening agents for sugarcane are produced.

As an alternative, compound (I) can be readily converted to an amino-amide, 2-amino-3-carbamido-4,5-tetramethylenethiophene. Such a compound is disclosed as (IIIa) by Arya in Indian Journal of Chemistry 10, 1141 (1972). As is otherwise well-known, in preparing this compound from compound (I) the necessary conversion of the cyano group to an amide group can be achieved by conventional mild aqueous hydrolysis. The resulting amino-amide, hereinafter referred to as compound (III), has a melting point of 175–7° C. and is suitable for use as a ripening agent for sugarcane. It can also be used as a starting material for the preparation of other derivatives by reaction of the amino group with other appropriate reactants, whereby other effective ripening agents for sugarcane may be produced.

The sugarcane ripeners which are preferred in the practice of this invention accordingly fall into three principal subclasses, to wit, the amine-nitrile substituted tetramethylenethiophenes of the formula

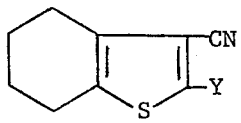, the amine-carboethoxy substituted tetramethylenethiophenes of the formula

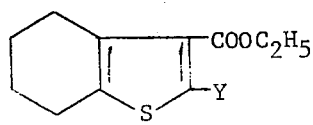

and the amine-carbamido substituted tetramethylenethiophenes of the formula

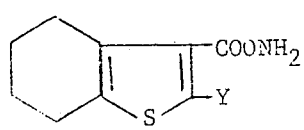

Representative of the useful compounds of the amine-nitrile subclass are those of the formula

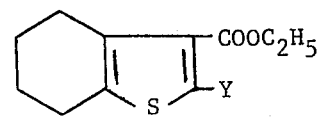

wherein Y is propionamido, 4-chloropropionamido, (5-chloro-2,4-dimethoxyphenyl)-thioureido or furan-2-carbamido.

Representative of the useful compounds of the amine-ester subclass of the formula are those wherein Y is amino, chloracetamido, propionamido, furoylamido, (3-trifluoromethylphenyl)-ureido, (3-chlorophenyl)-ureido, (4-fluorophenyl)-ureido, (2-methoxy-5-methylphenyl)-ureido or (2-chloro-5-trifluoromethylphenyl)-ureido.

In accordance with this invention, a sugarcane crop which is nearing the normal maturity stage is treated with a thiophene ripening agent of the kind disclosed above, or with a composition containing one or more of such ripening agents, about two to ten weeks before harvest, the preferred time for treatment being between about four and ten weeks prior to harvest.

Good results are obtained when the sugarcane crop is treated in the field at a rate in the range of from 1 to 4 pounds per acre (1 to 4 kg/hectare) of the active ripening agent. However, higher rates of chemical ripener, e.g., up to about 30 pounds per acre or more (30 kg/hectare or more) or rates lower than 1 pound per acre (1 kg/hectare) can also be used. The optimum amount will vary somewhat depending on the particular species of ripener used, the particular mode of application, evironmental conditions, time of year, and age and variety of cane being treated, but can be readily determined for each particular case by preliminary testing.

The active agent is conveniently applied in the field in the form of an aqueous solution, emulsion or suspension, i.e., in a liquid composition which may be sprayed onto the maturing cane plants from a boom-spray, or it can be dusted on from an airplane or the like as a dust composition which contains the active compound diluted with an inert solid such as clay.

In preparing suitable liquid compositions, surface active agents of the type described, for instance, in U.S. Pat. No. 3,224,865, column 2, lines 61–66 or in U.S. Pat. No. 3.245,775, column 2, lines 57–64 are convenient to use. The preferred surfactants for use in liquid compositions of the present invention are those of the non-ionic type, e.g., alkyl phenoxy poly(ethenoxy)ethanols such as adducts of nonyl-phenol and ethylene oxide; trimethyl nonyl polyethylene glycol ethers; polyethylene oxide adducts of fatty and resin acids, and long chain alkyl mercaptan adducts with ethylene oxide.

With the type of boom-spray apparatus used in this work, it has been found convenient to apply the active ripener to the sugarcane field in the form of an aqueous solution, suspension or emulsion having a concentration of active agent such that the application of the liquid composition at the rate of from 5 to 20 gallons per acre (about 50 to 200 liters/hectare) will provide the required dosage of active chemical. However, the use of lower or higher gallonages may be preferred when a different dispensing mechanism is used.

The preferred carrier for the active ripening agent is water to which about 0.1 to 2% by weight of surface active agent, i.e., wetting or emulsifying agent, has been added. However, instead of using water as the carrier, non-phytotoxic mineral oils either as such or in the form of water-in-oil or oil-in-water emulsions may be used similarly in accordance with practices which are otherwise well known in the art of treating vegetation in the field with beneficial growth control agents. Excellent results are obtained when the ripening agents of the present invention constitute essentially the sole active ingredient in the treating composition, but they may also be applied in combination with other agents.

DESCRIPTION OF SPECIFIC EMBODIMENTS

Example 1

Part A — Preparation of Treating Compositions a. A treating composition is prepared by weighing out 1 gram of compound (II), i.e., 2-amino-3-carboethoxy-4,5-tetramethylenethiophene, and dispersing it in approximately 6 ml of water. This mixture is diluted with water to exactly 8 ml and 1 drop of commercial Tergitol NPX (liquid) surfactant is added with a medicine dropper to the diluted liquid mixture. The resulting composition is agitated by shaking prior to application.

b. Another treating composition is prepared exactly as described above in (a), using compound (III), i.e., 2-amino-3-carbamido-4,5-tetramethylenethiophene, instead of compound (II).

Part B — Application of Compounds (II) and (III) to Cane

A 0.3 ml dose of the aqueous compositions containing 38 mg of the amino-ester compound (II) or the amino-amide compound (III), respectively, prepared as described in Part A above, is applied on the spindle area at the top of the last visible dewlap of each of 20 stalks of sugarcane in a test plot in a commercial cane field in Hawaii, using a syringe with a fine needle as a microapplicator.

Other groups of 20 stalks each in the same test plot are treated in an identical manner for comparative purposes with "Trysben" (dimethylamine salt of 2,3,6-trichlorobenzoic acid), used as a standard because of its known and consistent good activity.

The age of the cane at the time of application was 20.75 months.

A set of 10 of these treated stalks from each group were harvested 4 weeks after such treatment and another set of 10 were harvested 5 weeks after such treatment. At each harvest a set of 10 untreated stalks from the same plot were also harvested as a control.

The top 15 joints of each 10-stalk set of the treated stalks, as well as those of untreated control stalks from the same test plot, were removed, and each set is combined and analyzed in terms of juice purity and pol percent cane, following the so-called "press method" developed by T. Tanimoto, Hawaiian Planters' Record, 57, 133 (1964). "Pol percent cane" is a polarimetric determination and equals the percentage of sucrose if sucrose is the only optically active substance in the solution. In any event, determination of the pol percent cane is a standard and effective method for determining the sucrose content of sugarcane. The test data are given in Table I.

The data show that both compound (II) and compound (III) bring about a major increase in sucrose yield as compared with the untreated cane when these ripeners are applied 5 weeks prior to harvest. Both are about equally effective and only somewhat less effective than the standard ripener, Trysben. When application precedes harvest by only 4 weeks, the amino-amide compound (III) was considerably more effective than the amino-ester compound (II) in this particular test. However, in other tests which are not reported here the amino-ester compound (II) also proved to be a valuable ripener even when applied only 4 weeks before harvest. In two such other tests treatment with compound (II) resulted in raising the pol percent cane of the treated cane 39% and 52%, respectively, above that of the untreated control after a 4-week interval, and 44% and 26%, respectively, above that of the untreated control after a 5-week interval.

TABLE I

| Cane Variety: | 50-7209, Field 260 |
| Age: | 20.75 months |
| Date of Treatment: | June 12, Year X |
| Dates of Harvest: | July 10 and July 17, Year X |

| | Harvest Time After Treatment | | | |
| --- | --- | --- | --- | --- |
| | 4 Weeks | | 5 Weeks | |
| Ripening Agent | Juice Purity | Pol % Cane | Juice Purity | Pol % Cane |
| Amino-Ester Compound (II), 38 mg/stalk | 69.08 | 6.50 | 78.96 | 9.76 |
| Amino-Amide Compound (III), 38 mg/stalk | 69.21 | 8.01 | 77.93 | 9.63 |
| Trysben (standard) | 72.53 | 8.43 | 81.41 | 10.58 |
| Control (untreated) | 66.64 | 7.33 | 72.59 | 7.45 |

Example 2

In this example 2-propionamido-3-cyano-4,5-tetramethylenethiophene, hereinafter referred to as compound (XX), was applied to a crop of sugarcane and the cane stalks were harvested five weeks later. The procedure and dosage used were the same as described hereinabove in Example 1. The test data are shown in Table II, below.

Compound (XX) used in this example was prepared by mixing 17.8 g of compound (I) in 100 ml acetone and in the presence of 8 g pyridine with 13 g propionic anhydride, gently heating the mixture to obtain solution, and allowing to stand overnight. The mixture was then poured into an excess of ice water and the resulting white, crystalline solid (m.p. 138°–140° C.) was recovered by filtration and drying.

As Table II shows, the ripening effect of compound (XX) applied to the crop five weeks before harvest, was significantly more effective than that of Trysben under the same conditions and resulted in an important improvement in sucrose yield as compared with the untreated control.

Example 3

Using the same procedure as that described in Example 1 above, a number of other condensed thiophene compounds were tested in a series of different field tests as ripeners for sugarcane and compared with Trysben. Representative test data are shown in Tables III-A, III-B, III-C and III-D.

TABLE II

| Cane Variety: | 59-3775, Field 19 |
| --- | --- |
| Age: | 18.5 months |
| Date of Treatment: | December 9, Year Y |
| Date of Harvest: | January 22, Year Y + 1 |

| | Harvest Time 5 Weeks After Treatment | |
| --- | --- | --- |
| Ripening Agent | Juice Purity | Pol % Cane |
| Compound (XX)*, 38 mg/stalk | 77.42 | 9.83 |
| Trysben (standard) | 75.45 | 9.17 |
| Control (untreated) | 69.86 | 7.18 |

*2-propionamido-3-cyano-4,5-tetramethylenethiophene

Referring to Tables III-A, III-B and III-C, it can be seen that all the various condensed thiophenes tested show at least about the same degree of effectiveness as Trysben and that the two furan derivatives, Compounds (XI) and (XII), actually show a very significantly greater improvement in sucrose yield than Trysben has produced. Referring to Table III-D, it can be observed that Compounds VI and VIII brought about a very substantial increase in the sucrose yield over that obtained with the untreated cane under the same circumstances, regardless of whether the cane was harvested four or five weeks after treatment. Compound VII gave no worthwhile improvement under the particular conditions employed in this test. In the case of Compounds IX and X a significant increase in sucrose yield over that obtained in naturally maturing cane was obtained when harvest followed four weeks after treatment, but this advantage disappeared when the cane was allowed to ripen an additional week before harvest.

TABLE III-A

| Cane Variety: | 59-3775, Field 48 |
| --- | --- |
| Age: | 23 months |
| Date of Treatment: | August 7, Year Y |
| Dates of Harvest: | September 3 and September 10, Year Y |

| | Harvest Time After Treatment | | | |
| --- | --- | --- | --- | --- |
| | 4 Weeks | | 5 Weeks | |
| Ripening Agent | Juice Purity | Pol % Cane | Juice Purity | Pol % Cane |
| Compound (V)*, 38 mg/stalk | 64.48 | 11.09 | 74.45 | 9.52 |
| Trysben (standard) | 72.73 | 11.94 | 74.01 | 9.14 |
| Control (untreated) | 63.98 | 9.57 | 68.25 | 7.85 |

*Compound (V), 2-(5-chloro-2,4-dimethoxyphenyl)-thioureido-3-cyano-4,5-tetramethylenethiophene; prepared from 8.9 g of compound (I) and 11.45 g of 5-chloro-2,4-dimethoxyphenylisothiocyanate in 150 ml acetone, as more fully described in Example 3 in companion patent application Serial No. 589,401, which description is hereby incorporated herein by reference.

TABLE III-B

| Cane Variety: | 59-3775, Field 19 |
| --- | --- |
| Age: | 18.25 months |
| Date of Treatment: | December 10, Year Y |
| Date of Harvest: | January 7, Year Y + 1 |

| | Harvest Time 4 Weeks After Treatment | |
| --- | --- | --- |
| Ripening Agent | Juice Purity | Pol % Cane |
| Compound (XI)*, 38 mg/stalk | 82.42 | 10.87 |
| Trysben (standard) | 73.54 | 8.77 |
| Control (untreated) | 69.40 | 7.23 |

*Compound (XI), 2-(furan-2-carbamido)-3-cyano-4,5-tetramethylene-thiophene; prepared from compound (I) and 2-furoyl chloride, as more fully described in Example 9 of companion patent application Serial No. 589,401, which description is hereby incorporated herein by reference.

TABLE III-C

| Cane Variety: | 59-3775, Field 19 |
| --- | --- |
| Age: | 18.25 months |
| Date of Treatment: | December 13, Year Y |
| Date of Harvest: | January 17, Year Y + 1 |

| | Harvest Time 5 Weeks After Treatment | |
| --- | --- | --- |
| Ripening Agent | Juice Purity | Pol % Cane |
| Compound (XII)*, 38 mg/stalk | 81.90 | 11.05 |
| Trysben (standard) | 73.42 | 8.31 |
| Control (untreated) | 75.79 | 8.47 |

*Compound (XII), 2-(furan-2-carbamido)-3-carboethoxy-4,5-tetra-methylenethiophene; prepared from compound (II) and 2-furoyl chloride as more fully described in Example 10 of companion application Serial No. 589,401, which description is hereby incorporated herein by reference.

TABLE III-D

Cane Variety: 59-3775, Field 19
Age: 20.75 months
Date of Treatment: February 28, Year Y 1 +
Dates of Harvest: March 27 and April 4, Year Y 1 +
Dosage of Ripener: 38 mg per stalk

| Compound | 4 Weeks | | 5 Weeks | |
| --- | --- | --- | --- | --- |
| | Juice Purity | Pol % Cane | Juice Purity | Pol % Cane |
| VI | 81.75 | 10.35 | 84.72 | 12.18 |
| VII | 77.07 | 9.68 | 81.29 | 10.85 |
| VIII | 80.91 | 10.87 | 83.60 | 11.69 |
| IX | 81.33 | 10.38 | 77.17 | 9.60 |
| X | 82.33 | 10.71 | 81.30 | 10.65 |
| Trysben (standard) | 78.77 | 10.32 | 83.76 | 11.75 |
| Control (untreated) | 78.47 | 9.42 | 81.48 | 10.27 |

Compound VI:2-(2-chloroacetamido)-3-carboethoxy-4,5-tetra-methylenethiophene; m.p. 102–5° C.
Compound VII:2-(3-chlorophenyl)-ureido-3-carboethoxy-4,5-tetramethylenethiophene; m.p. 162–4° C.
Compound VIII:2-(4-fluorophenyl)-ureido-3-carboethoxy-4,5-tetramethylenethiophene; m.p. 186–8° C.
Compound IX:2-(2-methoxy-5-methylphenyl)-ureido-3-carboethoxy-4,5-tetramethylenethiophene; m.p. 138–41° C.
Compound X:2-(2-chloro-3-trifluoromethylphenyl)-ureido-3-carboethoxy-4,5-tetramethylenethiophene; m.p. 187–9° C.

That is, the sucrose content of the untreated cane increased substantially during the fifth week whereas the sucrose content of the treated cane began to decrease during the fifth week in these two cases, illustrating the different potency of the various compounds. Possibly a smaller dosage, and hence a less rapid drying rate of the cane, could actually make Compounds IX and X more effective over a longer period.

Optimum ripener activity varies from compound to compound and may occur from three to over thirteen weeks after application. Moreover, some compounds show a broad plateau of maximum or near-maximum activity, a highly desirable characteristic, while other compounds exhibit a sharper peak. Specific dosage understandably also can have a significant effect on the magnitude of maximum activity as well as the relationship between activity and time after application. For all these reasons, it is advisable to determine by preliminary empirical tests the optimum conditions for the use of any given compound under any particular circumstances. Due to some peculiar reason which is not explainable at the moment, the standard ripener, Trysben, produced no useful effect in the series of tests summarized in Table III-C. By contrast, use of Compound (XII) in accordance with the present invention gave a very substantial improvement in sucrose yield in this same series of tests.

The nature, scope, utility and effectiveness of the present invention have been described and exemplified in the foregoing specification. However, these examples are not intended to be limiting. The true scope of the invention which is entitled to patent protection is particularly pointed out in the appended claims.

What is claimed is:

1. A process for modifying the ripening of maturing sugarcane plants which comprises applying to the cane plants at a time from 2 to 10 weeks prior to harvest a sucrose increasing amount of a ripening agent of the formula

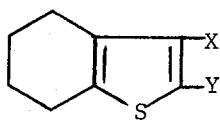

wherein X is cyano, carboethoxy or carbamido; Z is oxygen or sulfur; and Y is an amino radical -NH$_2$ or a radical having the formula

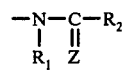

and in which radical R is $C_1 - C_4$ alkyl, $C_1 - C_4$ chlorinated alkyl, 2-furyl, or phenylamino containing up to three substituents on the benzene ring selected from the group consisting of $C_1 - C_4$ alkyl, $C_1 - C_4$ alkoxy, $C_1 - C_4$ chloroalkyl, $C_1 - C_4$ fluoroalkyl, fluorine or chlorine.

2. A process according to claim 1 wherein the ripening agent is applied to the plants as a liquid composition containing water as a carrier.

3. A process according to claim 1 wherein the cane plants are between 9 and 36 months of age when the ripening agent is applied thereto.

4. A process according to claim 3 wherein the ripening agent is of the formula

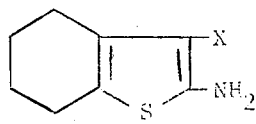

wherein X is carbamido or carboethoxy.

5. A process according to claim 3 wherein the ripening agent is 2-propionamido-3-cyano-4,5-tetramethylenethiophene.

6. A process according to claim 3 wherein the ripening agent is 2-(5-chloro-2,4-dimethoxyphenyl)-thioureido-3-cyano-4,5-tetramethylenethiophene.

7. A process according to claim 3 wherein the ripening agent is of the formula wherein X is cyano or carboethoxy and Y is furan-2-carbamido.

8. A process for modifying the ripening of field grown sugarcane plants so as to increase their yield of sucrose which comprises applying to the cane plants at a time from 2 to 10 weeks prior to harvest a sucrose increasing amount of a ripening agent of the formula

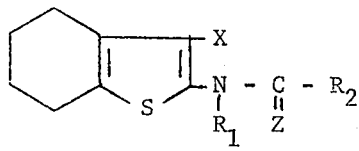

wherein X is cyano, a $C_1 - C_4$ carboalkoxy or a carbamido group, $R_1$ is hydrogen or methyl, Z is oxygen or sulfur and $R_2$ is $C_1 - C_4$ alkyl optionally substituted by chlorine, bromine or fluorine; or furyl

, or a phenylamino group containing up to three substituents on the benzene ring selected from the group consisting of $C_1 - C_4$ alkyl, $C_1 - C_4$ alkoxy, $C_1 - C_4$ haloalkyl, fluorine or chlorine.

9. A process according to claim 8 wherein said ripening agent is sprayed onto the cane plants as a liquid composition containing water as a carrier.

10. A process according to claim 9 wherein the aqueous composition contains between 0.1 and 2% by weight of a surface active agent.

11. A process according to claim 9 wherein the aqueous composition contains between 0.1 and 2% by weight of a non-ionic surface active agent.

* * * * *

UNITED STATES PATENT OFFICE
CERTIFICATE OF CORRECTION

Patent No. 3,989,505  Dated November 2, 1976

Inventor(s)  Louis G. Nickell

It is certified that error appears in the above-identified patent and that said Letters Patent are hereby corrected as shown below:

Amend lines 24-33 of column 12 to read as follows:

" wherein X is cyano, carboethoxy or carbamido; and Y is an amino radical - $NH_2$ or a radical having the formula $$- NH - \underset{\underset{Z}{\|}}{C} - R$$

and in which Z is oxygen or sulfur and radical R is $C_1 - C_4$ alkyl, $C_1 - C_4$ chlori-  "

Signed and Sealed this

First Day of March 1977

[SEAL]

Attest:

RUTH C. MASON  
*Attesting Officer*

C. MARSHALL DANN  
*Commissioner of Patents and Trademarks*